(12) United States Patent
Fujii et al.

(10) Patent No.: US 6,362,169 B1
(45) Date of Patent: Mar. 26, 2002

(54) ANTIBACTERIAL COMPOSITIONS WITH SYNERGISTIC EFFECT, DRUGS AND REMEDIES FOR DIGESTIVE DISEASES CONTAINING THE SAME, PROCESS FOR THE PRODUCTION THEREOF AND PREPARATIONS ASSOCIATED THEREWITH

(75) Inventors: Kenji Fujii, Akashi; Katsuji Yamashita, Kobe; Kazunori Hosoe, Takasago; Takayoshi Hidaka, Kobe, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/622,712

(22) PCT Filed: Feb. 17, 1999

(86) PCT No.: PCT/JP99/00717

§ 371 Date: Aug. 22, 2000

§ 102(e) Date: Aug. 22, 2000

(87) PCT Pub. No.: WO99/43327

PCT Pub. Date: Sep. 2, 1999

(30) Foreign Application Priority Data

Feb. 24, 1998 (JP) ............................................. 10-042418

(51) Int. Cl.$^7$ ...................... A61K 31/70; A61K 31/415; A61K 33/24
(52) U.S. Cl. .......................... 514/30; 514/394; 514/395; 424/653
(58) Field of Search .......................... 514/30, 394, 395; 424/653

(56) References Cited

U.S. PATENT DOCUMENTS 5,945,124 A * 8/1999 Sachs et al. ................. 424/472

FOREIGN PATENT DOCUMENTS

| JP | 7-126189 | | 5/1995 |
| WO | 9608259 | * | 3/1996 |
| WO | WO 97/02039 | | 1/1997 |
| WO | WO 97/09047 | | 3/1997 |

* cited by examiner

Primary Examiner—Kevin E. Weddington
(74) Attorney, Agent, or Firm—Armstrong, Westerman & Hattori, LLP

(57) ABSTRACT

Antibacterial compositions comprising (1) a rifamycin derivative represented by the formula (I) or its physiologically acceptable salt, and (2) a proton pump inhibitor (a) or a bismuth preparation (b) wherein the components (1) and (2) are used in such amounts as producing a synergistic effect against *Helicobacter pylori*, drugs and remedies for digestive organ diseases which contain the antibacterial compositions, process for producing them, and pharmaceutical preparations related to the antibacterial compositions. The compositions can be administered to patients with digestive diseases caused by infection of *Helicobacter pylori* in a smaller dose and at a lower administration frequency as compared with conventional remedies.

12 Claims, No Drawings

ANTIBACTERIAL COMPOSITIONS WITH SYNERGISTIC EFFECT, DRUGS AND REMEDIES FOR DIGESTIVE DISEASES CONTAINING THE SAME, PROCESS FOR THE PRODUCTION THEREOF AND PREPARATIONS ASSOCIATED THEREWITH

TECHNICAL FIELD

The present invention relates to an antibacterial composition against *Helicobacter pylori*. More particularly, the invention relates to drugs containing the antibacterial composition, remedies for diseases of digestive organs, e.g., gastritis, gastroduodenitis, erosive gastritis, gastric erosion, erosive duodenitis, gastric ulcer and duodenal ulcer, caused by the infection with *Helicobacter pylori* which is bacteria difficult to be eradicated by usual antibacterial materials such as antibiotics and synthetic antibacterial agents, a process for preparing them, and pharmaceutical preparations related to the antibacterial composition.

BACKGROUND ART

It is known that *Helicobacter pylori* is bacteria causing active chronic gastritis and is also greatly associated with gastric ulcer and duodenal ulcer. It is acknowledged that by eradication of infecting *Helicobacter pylori*, active chronic gastritis is cured and relapse of gastric ulcer and duodenal ulcer is remarkably decreased.

For treatment to eradicate *Helicobacter pylori*, there have been used, for example, antibacterial agents such as amoxicillin, ampicillin, clarithromycin, ofloxacin and tetracycline, bismuth preparations such as colloidal bismuth subcitrate and bismuth subsalicylate, antiprotozoals such as tinidazole and metronidazole, proton pump inhibitors such as omeprazole and lansoprazole, or drugs for gastrointestinal ulcer which are $H_2$ blocker such as cimetidine and ranitidine. At present, one or two are selected from the antibacterial agents, and one or two are selected from the bismuth preparations, the antiprotozoals and the drugs for gastrointestinal ulcer, and a combination of two or three agents selected from the respective groups is administered for the treatment.

However, such a combination has a relatively short duration of action and accordingly requires high doses and repeated administrations such as 3 or 4 times per day. Thus, there are problems that the administration is troublesome and adverse effect is easy to occur owing to high doses. These problems are considered to be caused by that the residence time of the administered agents in stomach is short and the antibacterial agent is low in antibacterial activity and is unstable under acidic condition in stomach.

On the other hand, with respect to rifamycin-related antibacterial agents, it is known that rifampicin, rifabutin and compounds involved in the present invention have an antibacterial activity to *Helicobacter pylori* (WO 97/09047, 1997). However, rifampicin is not suitable owing to high minimum inhibitory concentration (MIC). Rifabutin is known to exhibit a synergistic effect on minimum inhibitory concentration by combination use with a proton pump inhibitor or a bismuth preparation (WO 97/02039, 1997). However, synergistic effects under acidic condition corresponding to environment in stomach and on bactericidal activity have not been known. Also, there has not been known any effect of administration of a combination of a rifamycin derivative represented by formula (I) or its physiologically acceptable salt in the present invention with a proton pump inhibitor or a bismuth preparation.

DISCLOSURE OF INVENTION

As a result of making an intensive study in order to solve the above problems, the present inventors have found an antibacterial composition which shows synergistic effects on both the growth inhibitory activity and the bactericidal activity to *Helicobacter pylori* under an acidic environment and have made it clear that this antibacterial composition is effective for the treatment to eradicate *Helicobacter pylori*, thus they have accomplished the present invention.

That is to say, the present invention relates to an antibacterial composition comprising:

(1) a rifamycin derivative of the formula (I) or a physiologically acceptable salt thereof:

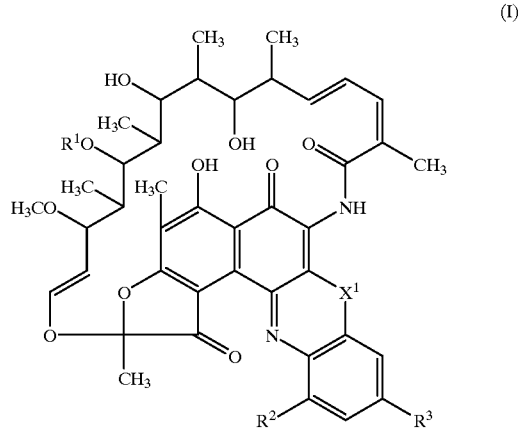

(I)

wherein
$X^1$ is an oxygen atom or a sulfur atom,
$R^1$ is an acetyl group or a hydrogen atom,
$R^2$ is a hydrogen atom, a hydroxyl group or an alkyl group having 1 to 3 carbon atoms, and
$R^3$ is a group of the formula:

wherein
$R^4$ and $R^5$ are the same or different and each is an alkyl group having 1 to 3 carbon atoms or a group of the formula:

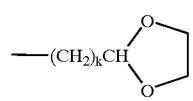

in which k is an integer of 1 to 3, a group of the formula:

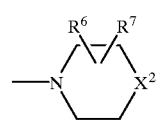

where in $R^6$ and $R^7$ are the same or different and each is a hydrogen atom or an alkyl group having 1 to 3 carbon atoms, and $X^2$ is an oxygen atom, a sulfur atom, a carbonyl group, a group of the formula:

in which $R^8$ and $R^9$ are the same or different and each is a hydrogen atom or an alkyl group having 1 to 3 carbon atoms, or $R^8$ and $R^9$ are joined to form a group: —$(CH_2)_l$— in which l is an integer of 1 to 4 or a group of the formula:

in which m is 0 or 1, $R^{10}$ is a hydrogen atom, an alkyl group having 1 to 6 carbon atoms or a group of the formula: —$(CH_2)_nX^3$ in which n is an integer of 1 to 4 and $X^3$ is an alkoxy group having 1 to 3 carbon atoms, a vinyl group, an ethynyl group or a group of the formula:

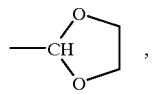

and (2) a proton pump inhibitor (a) or a bismuth preparation (b), wherein the components (1) and (2) are used in amounts producing a synergistic effect against *Helicobacter pylon* (Claim 1).

Further, the present invention relates to the antibacterial composition of Claim 1, wherein said rifamycin derivative (I) or its physiologically acceptable salt is a compound in which $X^1$ is an oxygen atom, $R^1$ is an acetyl group, $R^2$ is a hydroxyl group, and $R^3$ is 4-isobutylpiperazinyl group (Claim 2).

Further, the present invention relates to the antibacterial composition of Claim 1 or 2 wherein said proton pump inhibitor is a member selected from the group consisting of omeprazole, lansoprazole, leminoprazole, pantoprazole and robeprazole (Claim 3).

Further, the present invention relates to the antibacterial composition of Claim 3 wherein said proton pump inhibitor is lansoprazole (Claim 4).

Further, the present invention relates to the antibacterial composition of Claim 1 or 2, wherein said bismuth preparation is a member selected from the group consisting of colloidal bismuth subcitrate and bismuth subsalicylate (Claim 5).

Further, the present invention relates to the antibacterial composition of Claim 5, wherein said bismuth preparation is bismuth subsalicylate (Claim 6).

Further, the present invention relates to the antibacterial composition of any one of Claims 1 to 6, which is effective for the treatment to eradicate *Helicobacter pylori* (Claim 7).

The present invention relates to a drug containing (1) the antibacterial composition of any one of Claims 1 to 7 as an effective component, and (2) a pharmacologically acceptable carrier (Claim 8).

The present invention relates to a remedy for diseases of digestive organs containing (1) the antibacterial composition of any one of Claims 1 to 7 as effective component, and (2) a pharmaceutically acceptable carrier (Claim 9).

The present invention relates to a process for producing drugs which comprises mixing (1) the antibacterial composition of any one of Claims 1 to 7 and (2) a pharmacologically acceptable carrier (Claim 10).

The present invention relates to a process for producing remedies for diseases of digestive organs which comprises mixing (1) the antibacterial composition of any one of Claims 1 to 7 and (2) a pharmacologically acceptable carrier (Claim 11).

The present invention relates to a pharmaceutical preparation comprising:

(1) a rifamycin derivative of the formula (I) or a physiologically acceptable salt thereof:

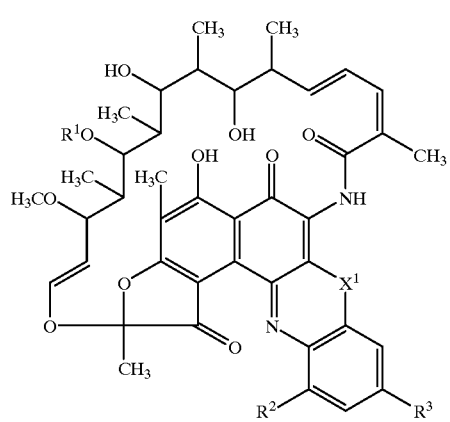

(I)

wherein
$X^1$ is an oxygen atom or a sulfur atom,
$R^1$ is an acetyl group or a hydrogen atom,
$R^2$ is a hydrogen atom, a hydroxyl group or an alkyl group having 1 to 3 carbon atoms, and
$R^3$ is a group of the formula:

wherein $R^4$ $R^5$ are the same or different and each is an alkyl group having 1 to 3 carbon atoms or a group of the formula:

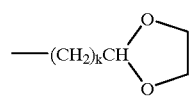

in which k is an integer of 1 to 3, a group of the formula:

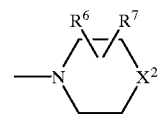

wherein $R^6$ and $R^7$ are the same or different and each is a hydrogen atom or an alkyl group having 1 to 3 carbon atoms, and $X^2$ is an oxygen atom, a sulfur atom, a carbonyl group, a group of the formula:

in which $R^8$ and $R^9$ are the same or different and each is a hydrogen atom or an alkyl group having 1 to 3 carbon atoms, or $R^8$ and $R^9$ are joined to form a group: —$(CH_2)_l$— in which l is an integer of 1 to 4 or a group of the formula:

in which m is 0 or 1, $R^{10}$ is a hydrogen atom, an alkyl group having 1 to 6 carbon atoms or a group of the formula: —$(CH_2)_n X^3$ in which n is an integer of 1 to 4 and $X^3$ is an alkoxy group having 1 to 3 carbon atoms, a vinyl group, an ethynyl group or a group of the formula:

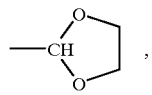

and (2) a proton pump inhibitor (a) or a bismuth preparation (b), wherein the components (1) and (2) are in a form suitable for simultaneous, separate or sequential administration in amounts producing a synergistic effect against *Helicobacter pylori* (Claim 12).

BEST MODE FOR CARRYING OUT THE INVENTION

In the formula (I), examples of the alkyl groups having 1 to 3 carbon atoms represented by $R^2$, $R^4$, $R^5$, $R^6$, $R^7$, $R^8$ and $R^9$ are methyl group, ethyl group, propyl group, isopropyl group and cyclopropyl group. The alkyl group having 1 to 6 carbon atoms represented by $R^{10}$ includes linear and cyclic alkyl groups such as methyl group, ethyl group, propyl group, isopropyl group, cyclopropyl group, butyl group, isobutyl group, sec-butyl group, tert-butyl group, cyclobutyl group, cyclopropylmethyl group, pentyl group, isopentyl group, sec-pentyl group, tert-pentyl group, cyclopentyl group, cyclobutylmethyl group, hexyl group, 4-methylpentyl group, cyclohexyl group and 3-methylcyclopentyl group. Examples of the alkoxy group having 1 to 3 carbon atoms represented by $X^3$ are methoxy group, ethoxy group, propoxy group, isopropoxy group and cyclopropoxy group.

The rifamycin derivatives of the formula (I) which can be used in the production of antibacterial compositions and remedies for diseases of digestive organs according to the present invention which are effective for the treatment to eradicate *Helicobacter pylori*, can be synthesized by the following methods.

That is to say, the rifamycin derivatives can be synthesized by the methods disclosed in JP-B-3-58352, JP-B-5-57275, JP-A-3-7291, JP-A-4-103589, JP-A-3-101689, JP-A-9-46753, Chem. Pharm. Bull., Vol. 41, 148(1993) and so on.

With respect to the physiologically acceptable salts of the rifamycin derivatives (I) which can be used in the production of antibacterial compositions according to the present invention effective for the treatment to eradicate *Helicobacter pylon*, physiologically acceptable salts can be selected from the salts (salts with bases or acids) disclosed in the above patent publications. Examples of the salts with bases are (1) metal salts, particularly salts with alkali metals and alkaline earth metals, (2) ammonium salts, and (3) amine salts, particularly salts with methylamine, ethylamine, diethylamine, triethylamine, pyrrolidine, morpholine, hexamethyleneimine and the like. Examples of the salts with acids are (1) salts with mineral acids such as sulfuric acid and hydrochloric acid, and (2) salts with organic acids such as p-toluenesulfonic acid, trifluroacetic acid and acetic acid.

The term "eradication of bacteria", "eradication of *Helicobacter pylori*" or the like as used herein means to decrease the number of bacteria existing in infected parts or to completely kill the bacterial.

Examples of the proton pump inhibitor which can be used in the production of antibacterial compositions according to the present invention effective for the treatment to eradicate *Helicobacter pylori* are, for instance, omeprazole, lansoprazole, leminoprazole, pantoprazole, robeprazole, and the like. Of these, lansoprazole is preferred. Also, the bismuth preparation means preparations containing a bismuth salt which can be used in the treatment of digestive diseases. Typical examples of the bismuth preparation are, for instance, bismuth subcitrate, bismuth subsalicylate, and the like. Bismuth subsalicylate is preferable.

The antibacterial composition of the present invention effective for the treatment to eradicate *Helicobacter pylori* is useful for drugs containing the composition, and remedies for digestive diseases such as gastritis, gastroduodenitis, erosive gastritis, gastric erosion, erosive duodenitis, gastric ulcer or duodenal ulcer which are caused by infection of *Helicobacter pylori*.

The antibacterial composition of the present invention effective for the treatment to eradicate *Helicobacter pylori* shows an antibacterial activity higher than the sum of the antibacterial activities of the individual components included therein, thus showing a marked synergistic effect.

Further, since the antibacterial composition of the present invention shows an excellent antibacterial activity against *Helicobacter pylori*, since it well reaches the affected part by oral administration, and since it is stable even under a low pH, the composition is suitable for the treatment to eradicate *Helicobacter pylori*.

Therefore, the antibacterial composition against *Helicobacter pylori* according to the present invention shows a sufficient effect even at small doses which are insufficient when the components are used individually. That is to say, since the antibacterial composition according to the present invention shows a better therapeutic effect than the individual antibacterial agents, it is more effective for the treatment of diseases caused by the infection of *Helicobacter pylori*.

It is well known that to avoid emergence of resistant strains against antibacterial agents, a combination use of a plurality of agents is desirable rather than a single use. From such a point of view, the antibacterial composition against *Helicobacter pylori* according to the present invention is particularly useful for long term therapy.

The present invention includes not only the above-mentioned antibacterial composition effective for the treatment to eradicate *Helicobacter pylori*, but also a drug and a remedy for digestive diseases which contain the antibacterial composition and an arbitrary pharmacologically acceptable carrier, and processes for producing the drug and the remedy by mixing the antibacterial composition with the carrier.

The drugs and remedies according to the present invention which contain as an effective component the antibacterial composition effective for the treatment to eradicate *Helicobacter pylori* can be in the form of oral pharmaceutical preparations such as powder, tablet, capsule, sugar coated tablet, granule and syrup.

As the carrier used in the drugs and remedies according to the present invention which contain as an effective component the antibacterial composition effective for the treatment to eradicate *Helicobacter pylori*, there are used organic or inorganic, solid or liquid pharmacologically acceptable carrier materials suitable for oral administration which are usually inactive.

The carriers encompass diluents, excipients, lubricants and the like which have been generally used in the preparations. Examples of the carrier are, for instance, crystalline cellulose, gelatin, lactose, starch, magnesium stearate, talc, vegetable or animal fats and oils, gum, polyalkylene glycol, and the like.

The proportion of the antibacterial composition, which is effective for the treatment to eradicate *Helicobacter pylori*, in the drugs and the remedies for digestive organ diseases according to the present invention can be varied within the range of 0.2 to 100% by weight based on the carrier.

Also, the remedies for digestive organ diseases of the present invention can contain other remedies for digestive organ diseases and other drugs, which are compatible with the antibacterial composition mentioned above. Needless to say, in this case, the antibacterial composition of the present invention effective for the treatment of *Helicobacter pylori* infection may not be a main component of that pharmaceutical preparation.

The above-mentioned respective components which show a synergistic effect may be mixed just before the administration. In that case, they can be presented in a form suitable for simultaneous, separate or sequential administration in the treatment of diseases caused by the infection of *Helicobacter pylori*.

Thus, the present invention also provides a pharmaceutical preparation comprising:

(1) a rifamycin derivative of the formula (I) or a physiologically acceptable salt thereof:

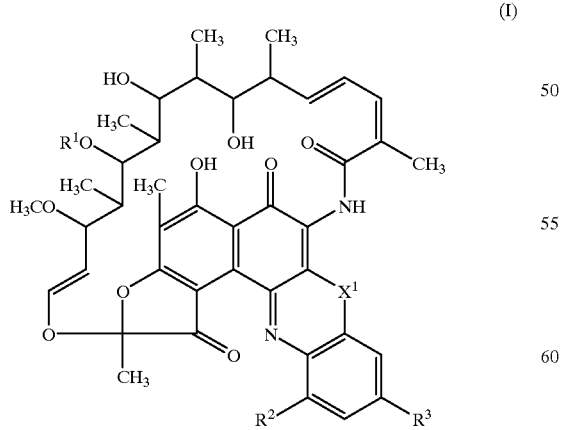

(I)

wherein
$X^1$ is an oxygen atom or a sulfur atom,
$R^1$ is an acetyl group or a hydrogen atom,
$R^2$ is a hydrogen atom, a hydroxyl group or an alkyl group having 1 to 3 carbon atoms, and
$R^3$ is a group of the formula:

wherein $R^4$ and $R^5$ are the same or different and each is an alkyl group having 1 to 3 carbon atoms or a group of the formula:

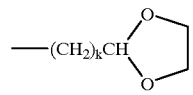

in which k is an integer of 1 to 3, a group of the formula:

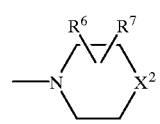

wherein $R^6$ and $R^7$ are the same or different and each is a hydrogen atom or an alkyl group having 1 to 3 carbon atoms, and $X^2$ is an oxygen atom, a sulfur atom, a carbonyl group, a group of the formula:

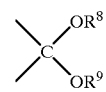

in which $R^8$ and $R^9$ are the same or different and each is a hydrogen atom or an alkyl group having 1 to 3 carbon atoms, or $R^8$ and $R^9$ are joined to form a group: —$(CH_2)_l$— in which l is an integer of 1 to 4 or a group of the formula:

in which m is 0 or 1, $R^{10}$ is a hydrogen atom, an alkyl group having 1 to 6 carbon atoms or a group of the formula: —$(CH_2)_n X^3$ in which n is an integer of 1 to 4 and $X^3$ is an alkoxy group having 1 to 3 carbon atoms, a vinyl group, an ethynyl group or a group of the formula:

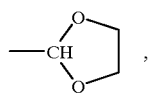

, and
(2) a proton pump inhibitor (a) or a bismuth preparation (b), wherein the components (1) and (2) are in a form suitable for simultaneous, separate or sequential administration in amounts producing a synergistic effect against *Helicobacter pylori* in the treatment of diseases caused by the infection of *Helicobacter pylori*.

The daily doses of individual components in the antibacterial composition according to the present invention are lower than the effective doses of the individual components required when used alone.

The weight ratio of the rifamycin derivative (I) or its physiologically acceptable salt to the proton pump inhibitor or bismuth preparation, which produces a synergistic effect against *Helicobacter pylori*, is from 1:100 to 100:1. Preferably, the weight ratio of the rifamycin derivative (I) or its physiologically acceptable salt to the proton pump inhibitor is from 30:1 to 1:1. Also, the weight ratio of the rifamycin derivative (I) or its physiologically acceptable salt to the bismuth preparation is preferably from 1:10 to 10:1.

When 1,000 mg of a combination of a compound A which is a rifamycin derivative (I) wherein $X^1$ is oxygen atom, $R^1$ is acetyl group, $R^2$ is hydroxyl group and $R^3$ is 4-isobutylpiperazinyl group, and bismuth subsalicylate, and 1,000 mg of a combination of the compound A and lansoprazole were orally administered to a mouse respectively, no toxicity was shown.

The antibacterial composition of the present invention effective for the treatment to eradicate *Helicobacter pylori* is generally administered in such a dose that desired effects are achieved without side-effects. Although the actual dose of the antibacterial composition should be determined by a doctor, the antibacterial composition is administered as a unit dosage preparation containing 1 mg to 5 g, preferably 3 mg to 1 g, of the antibacterial composition. For an adult the daily dose thereof is from 10 mg to 10 g, preferably from about 20 mg to about 5 g.

The present invention is more specifically explained by means of the following Test Examples and Examples.

TEST EXAMPLE 1

Assay of Antibacterial Action

Tests were carried out according to the measuring method for MIC (minimum inhibitory concentration) by liquid microdilution which was the standard method of The Japanese Society of Chemotherapy (Journal of the Japanese Society of Chemotherapy, Vol. 38, pp.102, 1990). The antibacterial action of assayed compounds was measured using *helicobacter pylori* ATCC 43504 which had been acknowledged as a standard strain. As a culture medium was used Brucella liquid medium containing 10% horse serum and adjusted to pH 7.0 or pH 5.5. About 5 μl of a cell suspension having a viable cell count of $10^7$/ml was inoculated into each of wells of a plate. After incubation at 37° C. for 5 days under a $CO_2$ concentration of 10%, the effect of eradicating the bacteria of the assayed compound was determined by the following equation (A). That is to say, a composition comprising components (1) and (2) which satisfied the equation (A) was determined as a composition having a synergistic effect. With respect to the minimum bactericidal concentration (MBC), about 5 μl of the medium obtained after the measurement of MIC was inoculated into a Columbia blood agar containing 5% horse serum and incubated in the same manner as in the measurement of MIC, and the minimum bactericidal concentration of the assayed compound was measured. Similarly with MIC, the synergistic effect on MBC was determined according to the following equation (B). That is to say, a composition comprising components (1) and (2) which satisfied the equation (B) was determined as a composition having a synergistic effect.

$$\frac{\text{Antibacterially active concentration of component (1)}}{\text{MIC of component(1)}} + \frac{\text{Antibacterially active concentration of component (2)}}{\text{MIC of component(2)}} < 1 \quad (A)$$

$$\frac{\text{Antibacterially active concentration of component (1)}}{\text{MBC of component(1)}} + \frac{\text{Antibacterially active concentration of component (2)}}{\text{MBC of component(2)}} < 1 \quad (B)$$

The drug concentrations (μg/ml) that show an antibacterial activity against *Helicobacter pylori*, measured according to the above testing method, are shown in the following Tables with respect to the compound A (component (1)) which is a rifamycin derivative (I) wherein $X^1$ is oxygen atom, $R^1$ is acetyl group, $R^2$ is hydroxyl group and $R^3$ is 4-isobutylpiperazinyl group, and lansoprazole or bismuth subsalicylate (component (2)) which are used alone or in combination thereof. In the following Tables, the antibacterial action of a single use of a compound is represented by minimum inhibitory concentration (μg/ml) and minimum bactericidal concentration (μg/ml). In case of a combination of components (1) and (2), the antibacterial action is represented by the concentration (μg/ml) of each of the components that showed an antibacterial activity.

Tables 1 to 4 show the results of the antibacterial action of antibacterial compositions comprising the compound A and bismuth subsalicylate.

As apparent from Tables 1 and 2, the inhibiting drug concentrations of a combination of the compound (A) and bismuth subsalicylate are much lower than a single use of each thereof in both neutral environment and acidic environment. Thus, it is found that the combined drug has a synergistic effect.

Table 3 shows the results of MBC of an antibacterial composition comprising the compound A and bismuth subsalicylate under neutral condition.

Table 4 shows the results of MBC of an antibacterial composition comprising the compound A and bismuth subsalicylate under acidic condition.

As apparent from Tables 3 and 4, the bactericidal concentrations of a combination of the compound (A) and bismuth subsalicylate are much lower than a single use of each thereof in both neutral environment and acidic environment. Thus, it is found that the combined drug has a synergistic effect.

Table 5 shows the results of MIC of an antibacterial composition comprising the compound A and lansoprazole under neutral condition.

Table 6 shows the results of MIC of an antibacterial composition comprising the compound A and lansoprazole under acidic condition.

As apparent from Tables 5 and 6, the inhibiting drug concentrations of a combination of the compound (A) and lansoprazole are much lower than a single use of each thereof in both neutral environment and acidic environment. Thus, it is found that the combined drug has a synergistic effect.

Table 7 shows the results of MBC of an antibacterial composition comprising the compound A and lansoprazole under neutral condition.

Table 8 shows the results of MBC of an antibacterial composition comprising the compound A and lansoprazole under acidic condition.

As apparent from Tables 7 and 8, the bactericidal concentrations of a combination of the compound (A) and lansoprazole are much lower than a single use of each thereof in both neutral environment and acidic environment. Thus, it is found that the combined drug has a synergistic effect.

TABLE 1 neutral (pH 7.0)

| Compound A (µg/ml) | Bismuth subsalicylate (µg/ml) | Judgement |
|---|---|---|
| 0.004 | — | (MIC) |
| — | 2 | (MIC) |
| 0.001 | 1 | Synergistic effect |
| 0.001 | 0.5 | Synergistic effect |

TABLE 2 acidic (pH 5.5)

| Compound A (µg/ml) | Bismuth subsalicylate (µg/ml) | Judgement |
|---|---|---|
| 0.002 | — | (MIC) |
| — | 2 | (MIC) |
| 0.0005 | 1 | Synergistic effect |
| 0.0005 | 0.5 | Synergistic effect |

TABLE 3 neutral (pH 7.0)

| Compound A (µg/ml) | Bismuth subsalicylate (µg/ml) | Judgement |
|---|---|---|
| 0.008 | — | (MBC) |
| — | 2 | (MBC) |
| 0.004 | 0.5 | Synergistic effect |

TABLE 4 acidic (pH 5.5)

| Compound A (µg/ml) | Bismuth subsalicylate (µg/ml) | Judgement |
|---|---|---|
| 0.008 | — | (MBC) |
| — | 2 | (MBC) |
| 0.002 | 1 | Synergistic effect |
| 0.002 | 0.5 | Synergistic effect |

TABLE 5 neutral (pH 7.0)

| Compound A (µg/ml) | Lansoprazole (µg/ml) | Judgement |
|---|---|---|
| 0.004 | — | (MIC) |
| — | 2 | (MIC) |
| 0.001 | 1 | Synergistic effect |
| 0.001 | 0.5 | Synergistic effect |

TABLE 6 acidic (pH 5.5)

| Compound A (µg/ml) | Lansoprazole (µg/ml) | Judgement |
|---|---|---|
| 0.002 | — | (MIC) |
| — | 2 | (MIC) |
| 0.0005 | 1 | Synergistic effect |
| 0.0005 | 0.5 | Synergistic effect |

TABLE 7 neutral (pH 7.0)

| Compound A (µg/ml) | Lansoprazole (µg/ml) | Judgement |
|---|---|---|
| 0.016 | — | (MBC) |
| — | 2 | (MBC) |
| 0.008 | 0.5 | Synergistic effect |
| 0.004 | 1 | Synergistic effect |

TABLE 8 acidic (pH 5.5)

| Compound A (µg/ml) | Lansoprazole (µg/ml) | Judgement |
|---|---|---|
| 0.008 | — | (MBC) |
| — | 2 | (MBC) |
| 0.004 | 0.5 | Synergistic effect |

EXAMPLE 1

A mixture of 100 g of compound A used in Test Example 1 which was a rifamycin derivative, 10 g of lansoprazole, 45 g of lactose and 41 g of dry potato starch was kneaded with 20 ml of water. The mixture was passed through a 16 mesh screen and dried at 40° C. to give granules. The granules were then uniformly mixed with 4 g of magnesium stearate and compressed by a conventional method into tablets each having a weight of 100 mg and containing 50 mg of compound A and 5 mg of lansoprazole per a tablet.

EXAMPLE 2

The procedure of Example 1 was repeated except that bismuth subsalicylate was used instead of lansoprazole, to give tablets each having a weight of 100 mg and containing 50 mg of compound A and 5 mg of bismuth subsalicylate per a tablet.

INDUSTRIAL APPLICABILITY

The antibacterial composition of the present invention comprising (1) a rifamycin derivative represented by the formula (I) or its physiologically acceptable salt, and (2) a proton pump inhibitor or a bismuth preparation wherein the components (1) and (2) are used in amounts producing a synergistic effect against *Helicobacter pylori,* shows a synergistic effect against diseases caused by infection of *Helicobacter pylori* and, therefore, it can be administered in a smaller dose and a decreased number of administrations.

What is claimed is:

1. An antibacterial composition comprising:
(1) a rifamycin derivative of the formula (I) or a physiologically acceptable salt thereof:

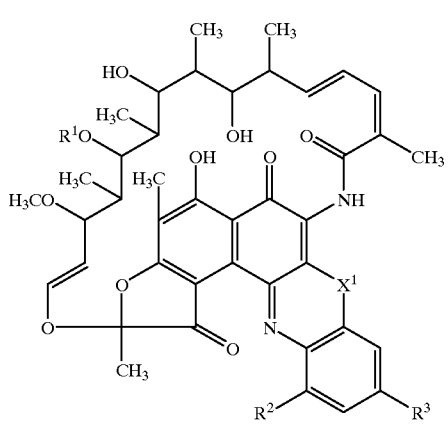

wherein
$X^1$ is an oxygen atom or a sulfur atom,
$R^1$ is an acetyl group or a hydrogen atom,
$R^2$ is a hydrogen atom, a hydroxyl group or an alkyl group having 1 to 3 carbon atoms, and

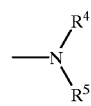

wherein $R^4$ and $R^5$ are the same or different and each is an alkyl group having 1 to 3 carbon atoms or a group of the formula:

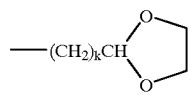

in which k is an integer of 1 to 3, a group of the formula:

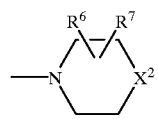

wherein $R^6$ and $R^7$ are the same or different and each is a hydrogen atom or an alkyl group having 1 to 3 carbon atoms, and $X^2$ is an oxygen atom, a sulfur atom, a carbonyl group, a group of the formula:

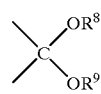

in which $R^8$ and $R^9$ are the same or different and each is a hydrogen atom or an alkyl group having 1 to 3 carbon atoms, or $R^8$ and $R^9$ are joined to form a group: —(CH$_2$)$_l$— in which l is an integer of 1 to 4 or a group of the formula:

in which m is 0 or 1, $R^{10}$ hydrogen atom, an alkyl group having 1 to 6 carbon atoms or a group of the formula: —(CH$_2$)$_n$X$^3$ in which n is an integer of 1 to 4 and $X^3$ is an alkoxy group having 1 to 3 carbon atoms, a vinyl group, an ethynyl group or a group of the formula:

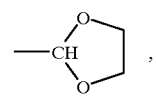

and (2) a proton pump inhibitor (a) or a bismuth preparation (b), wherein the components (1) and (2) are used in amounts producing a synergistic effect against *Helicobacter pylori*.

2. The antibacterial composition of claim 1, wherein said rifamycin derivative (I) or its physiologically acceptable salt is a compound in which $X^1$ is an oxygen atom, $R^1$ is an acetyl group, $R^2$ is a hydroxyl group, and $R^3$ is 4-isobutylpiperazinyl group.

3. The antibacterial composition of claim 1 or 2, wherein said composition includes said proton pump inhibitor and said proton pump inhibitor is a member selected from the group consisting of omeprazole, lansoprazole, leminoprazole, pantoprazole and robeprazole.

4. The antibacterial composition of claim 3, wherein said proton pump inhibitor is lansoprazole.

5. The antibacterial composition of claim 1 or 2, wherein said composition includes said bismuth preparation and said bismuth preparation is a member selected from the group consisting of colloidal bismuth subcitrate and bismuth subsalicylate.

6. The antibacterial composition of claim 5, wherein said bismuth preparation is bismuth subsalicylate.

7. The antibacterial composition of any one of claim 1, which is effective for the treatment to eradicate *Helicobacter pylori*.

8. A drug containing (1) the antibacterial composition of claim 1 or 2 as an effective component, and (2) a pharmacologically acceptable carrier.

9. A remedy for diseases of digestive organs containing (1) the antibacterial composition of claim 1 or 2 as an effective component, and (2) a pharmacologically acceptable carrier.

10. A process for producing drugs which comprises mixing (1) the antibacterial composition of claim 1 or 2 and (2) a pharmacologically acceptable carrier.

11. A process for producing remedies for diseases of digestive organs which comprises mixing (1) the antibacterial composition of claim 1 or 2 and (2) a pharmacologically acceptable carrier.

12. A pharmaceutical preparation comprising:
(1) a rifamycin derivative of the formula (I) or a physiologically acceptable salt thereof:

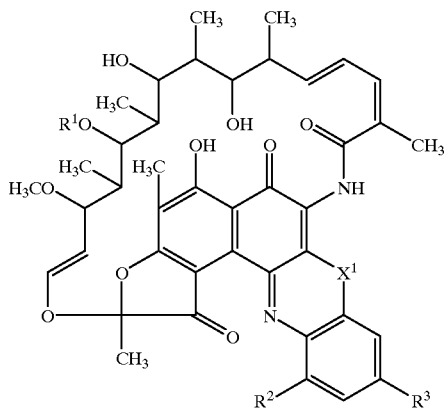 (I)

wherein $X^1$ is an oxygen atom or a sulfur atom, $R^1$ is an acetyl group or a hydrogen atom, $R^2$ is a hydrogen atom, a hydroxyl group or an alkyl group having 1 to 3 carbon atoms, and $R^3$ is a group of the formula:

wherein $R^4$ and $R^5$ are the same or different and each is an alkyl group having 1 to 3 carbon atoms or a group of the formula:

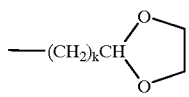

in which k is an integer of 1 to 3, a group of the formula:

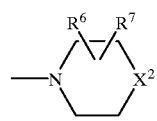

wherein $R^6$ and $R^7$ are the same or different and each is a hydrogen atom or an alkyl group having 1 to 3 carbon atoms, and $X^2$ is an oxygen atom, a sulfur atom, a carbonyl group, a group of the formula:

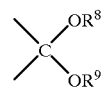

in which $R^8$ and $R^9$ are the same or different and each is a hydrogen atom or an alkyl group having 1 to 3 carbon atoms, or $R^8$ and $R^9$ are joined to form a group: —$(CH_2)_l$— in which l is an integer of 1 to 4 or a group of the formula:

in which m is 0 or 1, $R^{10}$ is a hydrogen atom, an alkyl group having 1 to 6 carbon atoms or a group of the formula: —$(CH_2)_nX^3$ in which n is an integer of 1 to 4 and $X^3$ is an alkoxy group having 1 to 3 carbon atoms, a vinyl group, an ethynyl group or a group of the formula:

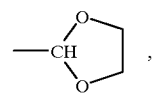, (2) a proton pump inhibitor (a) or a bismuth preparation (b), wherein the components (1) and (2) are in a form suitable for simultaneous, separate or sequential administration in amounts producing a synergistic effect against *Helicobacter pylori*.

* * * * *